(12) United States Patent
Taca, Jr.

(10) Patent No.: US 12,383,743 B2
(45) Date of Patent: Aug. 12, 2025

(54) TREATMENT OF ADDICTION AND DEPENDENCY

(71) Applicant: Arturo C. Taca, Jr., Creve Coeur, MO (US)

(72) Inventor: Arturo C. Taca, Jr., Creve Coeur, MO (US)

(*) Notice: Subject to any disclaimer, the term of this patent is extended or adjusted under 35 U.S.C. 154(b) by 822 days.

(21) Appl. No.: 17/519,738

(22) Filed: Nov. 5, 2021

(65) Prior Publication Data

US 2022/0072311 A1    Mar. 10, 2022

Related U.S. Application Data

(63) Continuation-in-part of application No. 15/918,720, filed on Mar. 12, 2018, now abandoned, which is a continuation-in-part of application No. PCT/US2016/051367, filed on Sep. 12, 2016.

(60) Provisional application No. 62/217,541, filed on Sep. 11, 2015.

(51) Int. Cl.
| | |
|---|---|
| *A61N 1/30* | (2006.01) |
| *A61K 31/4168* | (2006.01) |
| *A61K 31/55* | (2006.01) |
| *A61N 1/05* | (2006.01) |
| *A61N 1/36* | (2006.01) |
| *A61K 45/06* | (2006.01) |

(52) U.S. Cl.
CPC ....... *A61N 1/36089* (2013.01); *A61N 1/0526* (2013.01); *A61N 1/0568* (2013.01); *A61N 1/36053* (2013.01); *A61N 1/36189* (2013.01); *A61K 45/06* (2013.01)

(58) Field of Classification Search
CPC .......... A61N 1/32; A61N 1/328; A61K 31/55; A61K 31/4168; A61K 31/4355; A61K 31/495; A61K 31/137; A61K 31/551; A61K 31/5513; A61K 45/06; A61K 2300/00; A61P 25/36
See application file for complete search history.

(56) References Cited

U.S. PATENT DOCUMENTS 5,084,007 A * 1/1992 Malin ................ A61N 1/328
604/20
2008/0146549 A1* 6/2008 Coleman ............ A61K 31/551
514/401

* cited by examiner

*Primary Examiner* — Jon Eric C Morales
(74) *Attorney, Agent, or Firm* — Stinson LLP (57) ABSTRACT

The present invention relates to methods of treating or preventing addiction and relapse use of addictive agents where the method comprises: (a) administering to a subject a co-therapy treatment with an auricular or peri-auricular electro-acupuncture or neurostimulation device, (b) co-treatment with at least one non-narcotic detoxification agent and (c) administering to the subject an opioid antagonist. The methods and compositions of the invention are useful in the treatment or prevention of addiction to any agent, including alcohol, nicotine, marijuana, cocaine, and amphetamines, as well as compulsive and addictive behaviors, including pathological gambling and pathological overeating.

19 Claims, 1 Drawing Sheet

TREATMENT OF ADDICTION AND DEPENDENCY

CROSS-REFERENCE TO RELATED APPLICATIONS

The present Application for Patent is a continuation-in-part (CIP) of patent application Ser. No. 15/918,720 entitled "TREATMENT OF ADDICTION AND DEPENDENCY" filed Mar. 12, 2018, which claims the benefit of U.S. Provisional Application Ser. No. 62/217,541 entitled "TREATMENT OF ADDICTION AND DEPENDENCY" filed Sep. 11, 2015, and of PCT Application No. PCT/US16/51367 entitled "TREATMENT OF ADDICTION AND DEPENDENCY" filed Sep. 12, 2016, all of which are hereby expressly incorporated by reference herein to form part of the present disclosure.

BACKGROUND OF THE INVENTION

1. Field of the Invention

The field of art disclosed herein pertains to methods of treating or preventing addiction and relapse use of addictive agents, and treating or preventing addictive or compulsive behavior and relapse practice of an addictive behavior or compulsion. The methods of the present invention make use of an electrical stimulation device including a stimulator containing a generator for generating electrical stimulation pulses with defined stimulation parameters and a power supply for supplying the generator with electrical energy, and at least one needle electrode array for insertion into the skin surface of an area to be stimulated.

2. Description of the Related Art

The World Health Organization (WHO) defines substance addiction as using a substance repeatedly, despite knowing and experiencing harmful effects. Substance addiction is a chronic, relapsing disease characterized by a loss of control over drug use, compulsive drug seeking and craving for a substance, use that persists despite negative consequences, and physical and/or psychological dependence on the substance. Substance addiction typically follows a course of tolerance, withdrawal, compulsive drug taking behavior, drug seeking behavior, and relapse. Substance abuse and addiction are public health issues with significant social and economic impact on both the addict and society by playing a major role in violent crime and the spread of infectious diseases. Addictive substances include alcohol, caffeine, nicotine, cannabis (marijuana) and cannabis derivatives, opiates and other morphine-like opioid agonists such as heroin, phencyclidine and phencyclidine-like compounds, sedative ipnotics such as benzodiazepines and barbiturates and psychostimulants such as cocaine, amphetamines and amphetamine-related drugs such as dextroamphetamine and methylamphetamine.

According to the WHO, an estimated 13 million people abuse opiates worldwide, including 9 million heroin addicts. More than 25% of opiate abusers die from suicide, homicide, or an infectious disease, such as HIV and hepatitis, within 10-20 years of becoming addicted. Tolerance and physical dependence can develop within two to three days. While abuse and addiction to opioid agents is a known phenomenon, what is new is the worsening of this problem in the recent years (Compton and Volkow 2006; Compton and Volkow 2006). Epidemiological surveys of youth in the United States in 2003 indicated that opioid analgesics were among the most frequently abused illicit drugs among secondary students (12th graders), second only to marijuana (Delva et al. 2005). Furthermore, the past few years have seen a marked increase in the use of opioid medications in the United States and an even greater increase in problems associated with such use. This upsurge in use and problems is particularly concerning because it seems to represent an expanded pathway to opioid addiction (Siegal, Carlson et al. 2003). According to recent epidemiological data, 4.7% (i.e., 11.0 million) United States household residents over the age of twelve abused an opioid medication in 2002 and 13.7% of these persons (i.e., 1.5 million) endorsed the symptoms of a DSM-IV opioid use disorder (Association 1994; Substance Abuse and Mental Health Services Administration 2004). As recently reviewed by Compton and Volkow, the annual incidence of opioid analgesic abuse increased from 628,000 initiates in 1990 to 2.4 million initiates in 2001 (Administration 2003; Substance Abuse and Mental Health Services Administration 2003).

The goals for treatment of opiate addiction, as with other types of substance addictions, are to discontinue the use of the opiate while minimizing painful withdrawal symptoms and preventing relapse. Current treatments involve replacing the addictive drug with a substitution of an opioid receptor agonist or mixed agonist/antagonist. An alternative approach consists of the use of an opioid receptor antagonist to block the effect of the agonist. Antagonists provide no relief from pain or other withdrawal symptoms; rather, they can precipitate withdrawal, and their therapeutic use was associated with increased accidental opioid agonists overdosing and increased lethality. Use of agonists with a lower affinity for the receptors results in the least severe withdrawal symptoms, but it can lead to a dependence on the substitute opiate. Also, many substitution therapies take 3-6 months, allowing time for addicts to stop treatment midway.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, has been associated with reduced arrhythmia vulnerability following a myocardial infarction. Vagus nerve stimulation has been proposed to treat sleep disorders, gastrointestinal motility, eating disorders, obesity, anorexia, gastrointestinal tract disorders, hypertension, coma, and epilepsy.

Neural stimulation targeting other nerves has shown similar beneficial effect. Improved systems and methods for stimulating neural targets are needed. The present invention relates to methods of treatment for addiction using a device for the punctual stimulation of endings of nerves which are located in the region of the ears and run to the brainstem nuclei, said device having a battery-powered therapeutic current generator which is provided with an electronic circuit forming a low-frequency therapeutic current, and which device further has at least one stimulation needle electrode to be positioned at a nerve ending.

Aspects of the present disclosure are directed toward auricular nerve stimulation at terminals in one and/or both ear lobes, and based on events that are simultaneous, synchronous, in alternating sequences and/or with different off times, and to providing systems, apparatuses, and methods for application of stimulation for reproducible stimulation of the auricular nerve or nerves.

Aspects of the present disclosure are directed toward auricular nerve stimulation at terminals in one and/or both ear lobes, and based on events that are simultaneous, synchronous, in alternating sequences and/or with different off times, and to providing systems, apparatuses, and methods for application of stimulation for reproducible stimulation of the auricular nerve or nerves with minimal operator dependence.

Device, systems, methods and kits can be useful for auricular stimulation. One such device relates to auricular stimulation. The device includes one or two earpieces having an electrode arrangement configured and arranged to deliver a series of electrical stimulation signals to one or two auricular locations. One or two pulse-generator circuits is/are configured and arranged to generate the series of electrical stimulation signals having a stimulation profile, and deliver the electrical stimulation signals to the electrode arrangement. A sensor is configured and arranged to generate a feedback signal that is responsive to the electrical stimulation signals. A feedback circuit is configured and arranged to modify the stimulation profile in response to the feedback signal.

Device, systems, methods and kits that can be useful for auricular stimulation are generally known in the art. See, for example, U.S. Pat. Nos. 9,415,220; 9,061,148; 8,942,814; 8,731,672; 8,175,699; 8,010,197; 7,781,486; 7,725,188; 7,711,430; 7,660,637; 7,336,993; 7,200,444; 5,324,287.

Clearly, there is a need in the art for new methods for treating and preventing addiction and the relapse use of addictive agents. The present invention meets these needs by providing methods and pharmaceutical combinations useful in treating and preventing addiction and recidivism.

Certain embodiments of the present disclosure are directed towards methods of treatment using an auricular stimulation device that has an earpiece having an electrode and configured and arranged to deliver a series of electrical stimulation signals to a first auricular location of a particular individual based upon anatomical measurements from the particular individual. A pulse-generator circuit is configured and arranged to generate the series of electrical stimulation signals, and to deliver the electrical stimulation signals to the electrode.

The present invention provides for a system and methods not based upon acupuncture technique or "points" but rather peripheral nerve field stimulation, anatomical location of cranial nerves, peripheral nerves, arterial branches and/or neurovascular bundles, and energy transfer based upon accepted laws of energy transfer in human tissue. These physical entities can be selectively targeted by percutaneous implantation of one or more electrode-needle complex either with a single needle or an array connected to a generator set at a selected frequency or modulating frequency range.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

The present invention relates to the use of one or more non-narcotic detox medications used in combination with one or more auricular or peri-auricular electro-acupuncture or neurostimulation (e.g., a BRIDGE) device for the treatment and prevention of addictions and relapse to addictive use or behavior. Accordingly, the present invention provides methods and related compositions, unit dosage forms, and kits useful for the treatment and prevention of addictions, and for the treatment and prevention of relapse use of addictive agents or practice of addictive or compulsive behaviors.

In one embodiment, the present invention includes a method of treating or preventing an addiction, comprising determining that a subject has or is at risk of developing an addiction, and providing to the subject one or more non-narcotic detox medications used in combination with one or more auricular or peri-auricular electro-acupuncture or neurostimulation (e.g., a BRIDGE) device for a time effective for the treatment or prevention of the addiction.

In a related embodiment, the present invention provides a method of treating or preventing an addiction, comprising providing to a subject having an addiction one or more non-narcotic detox medications used in combination with one or more auricular or peri-auricular electro-acupuncture or neurostimulation (e.g., a BRIDGE) device and an additional therapeutic agent, wherein each of the one or more non-narcotic detox medications and the additional therapeutic agent contribute to the effective treatment or prevention of the addiction.

In one or more embodiments, the present invention provides for methods of treating drug or alcohol abuse, addiction or dependency in a subject, wherein the method comprises (a) administering to the subject a therapeutically effective amount of co-therapy for at least one day comprising treatment with an auricular or peri-auricular electro-acupuncture or neurostimulation device, (b) co-treatment for at least one day with the composition until a drug screen tests negative and then (c) administering to the subject a therapeutically effective amount of an opioid antagonist.

In one or more embodiments, the present invention provides for methods of treating drug or alcohol abuse, addiction or dependency comprising (a) administering to a subject in need thereof a therapeutically effective amount of co-therapy for at least one day comprising treatment with an auricular or peri-auricular electro-acupuncture or neurostimulation device, (b) co-treatment for at least one day with a composition comprising at least one non-narcotic detoxification agent and then (c) administering to a subject in need thereof a therapeutically effective amount of an opioid antagonist.

In one embodiment, the present invention provides for a composition comprising at least one non-narcotic detoxification agent for use in a method of treating drug or alcohol abuse, addiction or dependency in a subject, wherein the method comprises (a) administering to the subject a therapeutically effective amount of co-therapy for at least one day comprising treatment with an auricular or peri-auricular electro-acupuncture or neurostimulation device, (b) co-treatment for at least one day with the composition until a drug screen tests negative and then (c) administering to the subject a therapeutically effective amount of an opioid antagonist.

In one or more embodiments, the present invention provides for methods of treating an addiction or dependency in a subject, wherein the method comprises (a) treating a subject with an auricular or peri-auricular electro-acupuncture or neurostimulation device comprising one or more electrodes, wherein the electrodes are implanted and stimulated on the vagus nerve of the subject; which is followed by (b) administering to a subject in need thereof a therapeutically effective amount for at least one day with a composition consisting of at least one non-narcotic detoxification agent; and (c) administering to a subject in need thereof a therapeutically effective amount of an opioid antagonist.

In one or more embodiments, the present invention provides for methods of treating drug or alcohol abuse, addiction or dependency in a subject, wherein the method comprises (a) treating a subject with an electrical stimulation device comprising an auricular or peri-auricular electro-acupuncture or neurostimulation device comprising one or more electrodes, wherein the electrodes are implanted and stimulated on the vagus nerve of the subject; which is followed by (b) administering to a subject in need thereof a therapeutically effective amount for at least one day with a composition consisting of at least one non-narcotic detoxification agent including one of robaxin, pro-banthine, gabapentin, ropinirole, and trazodone; and (c) administering to a subject in need thereof a therapeutically effective amount of an opioid antagonist.

In one or more embodiments, the present invention provides for methods of treating drug or alcohol abuse, addiction or dependency in a subject, wherein the method comprises (a) treating a subject with an electrical stimulation device comprising an auricular or peri-auricular electro-acupuncture or neurostimulation device comprising one or more electrodes, wherein the electrodes are implanted and stimulated on the right-side vagus nerve of the subject; which is followed by (b) administering to a subject in need thereof a therapeutically effective amount for at least one day with a composition consisting of at least one non-narcotic detoxification agent including one of robaxin, pro-banthine, gabapentin, ropinirole, and trazodone, until a drug screen tests negative; and (c) administering to a subject in need thereof a therapeutically effective amount of an opioid antagonist.

In one or more embodiments, the present invention provides for methods of treating post-acute-withdrawal syndrome (PAWS), in a subject in need, wherein the method comprises administering to the subject a therapeutically effective amount of co-therapy for at least one day comprising (i) treatment with an auricular or peri-auricular electro-acupuncture or neurostimulation device, and (ii) co-treatment for at least one day with a composition comprising at least one non-narcotic detoxification agent.

In one or more embodiments, the present invention provides for methods of treating post-acute-withdrawal syndrome (PAWS), in a subject, wherein the method comprises (a) administering to the subject a therapeutically effective amount of co-therapy for at least one day comprising (i) treatment with an auricular or peri-auricular electro-acupuncture or neurostimulation device, and (ii) co-treatment for at least one day with a composition comprising at least one non-narcotic detoxification agent until symptoms subside and then (b) administering to the subject a therapeutically effective amount of an opioid antagonist.

In one or more embodiments, the present invention provides for methods of treating post-acute-withdrawal syndrome (PAWS), comprising (a) administering to a subject in need thereof a therapeutically effective amount of co-therapy for at least one day comprising treatment with an auricular or peri-auricular electro-acupuncture or neurostimulation device, (b) co-treatment for at least one day with a composition comprising at least one non-narcotic detoxification agent until sufficient reduction of symptoms and then (c) administering to a subject in need thereof a therapeutically effective amount of at least one non-narcotic detoxification agent.

In one embodiment, the present invention provides for a composition comprising at least one non-narcotic detoxification agent for use in a method of treating post-acute-withdrawal syndrome (PAWS), in a subject, wherein the method comprises (a) administering to the subject a therapeutically effective amount of co-therapy for at least one day comprising treatment with an auricular or peri-auricular electro-acupuncture or neurostimulation device, (b) co-treatment for at least one day with the composition and then (c) administering to the subject a therapeutically effective amount of an opioid antagonist.

In one or more embodiments, the present invention provides for methods of treating post-acute-withdrawal syndrome (PAWS), in a subject, wherein the method comprises (i) treating a subject with an electrical stimulation device comprising an auricular or peri-auricular electro-acupuncture or neurostimulation device comprising one or more electrodes, wherein the electrodes are implanted and stimulated on the vagus nerve of the subject; which is followed by, (ii) administering to a subject in need thereof a therapeutically effective amount for at least one day with a composition consisting of at least one non-narcotic detoxification agent; wherein the electrical stimulation device comprising an electrical signal generator configured to generate electrical stimulation pulses having a repetition frequency of 0.5 to 100 Hz and a duty cycle of 10 to 90%.

In one or more embodiments, the present invention provides for methods of treating post-acute-withdrawal syndrome (PAWS), in a subject, wherein the method comprises (i) treating a subject with an electrical stimulation device comprising an auricular or peri-auricular electro-acupuncture or neurostimulation device comprising one or more electrodes, wherein the electrodes are implanted and stimulated on the right-side vagus nerve of the subject; which is followed by, (ii) administering to a subject in need thereof a therapeutically effective amount for at least one day with a composition consisting of at least one non-narcotic detoxification agent, including one of robaxin, pro-banthine, gabapentin, ropinirole, and trazodone; wherein the electrical stimulation device comprising an electrical signal generator configured to generate electrical stimulation pulses having a repetition frequency of 0.5 to 100 Hz and a duty cycle of 10 to 90%, and wherein both steps (i) and (ii) treatment are carried out for about 1 to about 7 days.

In one embodiment, the present invention provides for any of the methods described herein wherein the method is performed by sequential or consecutive steps.

In one embodiment, the present invention provides for methods of treating post-acute-withdrawal syndrome (PAWS), in a subject, and broadly, a method of treating drug or alcohol abuse, addiction or dependency or preventing relapse use of drug or alcohol or addictive behavior, performed by sequential or consecutive steps, and not concomitantly.

In one or more embodiments, the present invention provides for sequential methods of treating drug or alcohol abuse, addiction or dependency or preventing relapse use of drug or alcohol or addictive behavior comprising: (a) treating a subject with an electrical stimulation device comprising an auricular or peri-auricular electro-acupuncture or neurostimulation device comprising one or more electrodes, wherein the electrodes are implanted and stimulated on the vagus nerve of the subject, which is followed by, (b) administering to a subject in need thereof a therapeutically effective amount for at least one day with a composition consisting of at least one non-narcotic detoxification agent, and (c) administering to a subject in need thereof a therapeutically effective amount of an opioid antagonist.

In one or more embodiments, the methods further comprise wherein the electrical stimulation device comprising an electrical signal generator configured to generate electrical stimulation pulses having a repetition frequency of 0.5 to 100 Hz and a duty cycle of 10 to 90%, and wherein both steps (a) and (b) treatment are carried out for about 1 to about 7 days.

In one or more embodiments, the main goal is to transition onto opioid antagonist (naltrexone) therapy however this protocol can be utilized in persons having difficulty with opioid partial-agonist therapy (buphrenorphine) during induction. Previous methods focused only on the transition to naltrexone products. In one or more embodiments, the present invention provides for using transcranial stimulation as a means to comfortably transition onto buprenorphine products. In one or more embodiments, the present invention provides for using the methods disclosed herein is to use transcranial stimulation in persons stabilized on high doses of opioid pain medications and reducing or sparing opioids over a period of time. The CDC has recommended cautious use of opioid pain medication and that persons over 90 mg morphine equivalent per day may not provide added pain control and increase risk of overdose. In one or more embodiments, the present invention provides for a way to reduce high doses morphine equivalent per day and achieve reasonable pain relief below 90 mg morphine equivalent without the added risks.

It has been widely accepted that transitioning onto an opioid antagonist, naltrexone, after detoxification is difficult and challenging. It is also widely accepted that during opioid withdrawal that it is easier to transition to opioid agonists, methadone, or partial agonists, buphrenorphine, because both do not require complete detoxification to an opioid free state to initiate treatment. If successfully transitioned to a replacement opioid like methadone or buphrenorphine products, individuals unfortunately are not free of the dependence of the opioid molecule. Because of the similar structures to heroin or prescription drugs like oxycontin, methadone and buphrenorphine both have similar risks in terms of physical dependence, diversion of the medications, misuse, respiratory depression, and death from overdose. For individuals interested in transitioning onto naltrexone products such as vivitrol, complete detoxification is required. If this process is not achieved a painful precipitated withdrawal syndrome can occur. A delay onto naltrexone products such as Vivitrol after detoxification is a clinical worry because of risk of overdose and death during periods of attempting to become completely abstinent from opioids. VIVITROL® is a brand-name drug of naltrexone for extended-release injectable suspension, which is supplied as a microsphere formulation of naltrexone for suspension, to be administered by intramuscular injection. Naltrexone is an opioid antagonist with little, if any, opioid agonist activity.

Researchers who studied this issue and published their report in the Lancet-Comparative effectiveness of extended-release naltrexone versus buprenorphine-naloxone for opioid relapse prevention (X: BOT): a multicenter, open-label, randomized controlled trial, concluded "In this population it is more difficult to initiate patients to XR-NTX than BUP-NX, and this negatively affected overall relapse. However, once initiated, both medications were equally safe and effective. Future work should focus on facilitating induction to XR-NTX and on improving treatment retention for both medications."

In one or more embodiments, the present invention provides for methods of treating post-acute-withdrawal syndrome (PAWS), in a subject, and broadly, a method of treating drug or alcohol abuse, addiction or dependency or preventing relapse use of drug or alcohol or addictive behavior, performed by sequential or consecutive steps, and not concomitantly. In one or more embodiments, there exists a relationship between the composition which is being administered to the subject and the treatment with the electrical stimulation device. For different types of compositions or drugs (which may be of same class or different class) and the treatment with the electrical stimulation device, the time period may and would certainly vary.

Withdrawal syndrome is a cluster of symptoms that occur for 1-2 weeks when a person stops taking an addictive or prescription drug. Some people take medications and do not become addicted to them but still experience withdrawal if they suddenly stop taking these medicines. Although withdrawal symptoms are uncomfortable, they typically end after two weeks at most, especially when a medical professional oversees the detox process. However, some drugs can lead to prolonged or protracted withdrawal, lasting for months and sometimes up to a year. People who consume a large amount of an intoxicating substance for a long time are more likely to develop this condition, which is called post-acute withdrawal syndrome (PAWS). It may take up to two years before neurochemistry returns to something resembling a normal state. After the acute stage of withdrawal ends, the post-acute stage begins, with an array of troubling symptoms. This period can last for 20 months or longer.

Post-acute-withdrawal syndrome (PAWS), or the terms post-withdrawal syndrome, protracted withdrawal syndrome, prolonged withdrawal syndromes describe a set of persistent impairments that occur after withdrawal from alcohol, opiates, benzodiazepines, antidepressants and other substances. Symptoms of PAWS are individual to each drug, but there are some common symptoms, including: Hostility or aggression; Anxiety, panic, or fear; Irritability and mood swings; Depression; Exhaustion or fatigue; and Inability to sleep. Other symptoms include: Psychosocial dysfunction, Anhedonia, Impaired interpersonal skills, Obsessive-compulsive behavior, Feelings of guilt, Autonomic disturbances, Pessimistic thoughts, Impaired concentration, Lack of initiative, Craving, Inability to think clearly, Memory problems, Emotional overreactions or numbness, Physical coordination problems, Stress sensitivity, Increased sensitivity to pain, Dreams of using substance.

In PAWS treatments, at least one narcotic-based detoxification agent may comprise one or more of buprenorphine (Suboxone), methadone, naltrexone, acamprosate, flumazenil and combinations thereof.

The syndrome may be in part due to persisting physiological adaptations in the central nervous system manifested in the form of continuing but slowly reversible tolerance, disturbances in neurotransmitters and resultant hyperexcitability of neuronal pathways.

The same neuronal pathways that are dysfunctional that cause the syndrome of PAWS are thoughts to be the targets of affect during peripheral nerve field stimulation. These pathways are stimulated using the similar neuroanatomy pathways that are identified during the treatment of opiate withdrawal namely: the autonomical nervous system, the neocortex the limbic system structures of the deep brain, the amygdala, and the spine.

Peripheral nerve field stimulators are safe and effective tools to rapidly reduce the signs and symptoms associated of Post-Acute Withdrawal Syndrome (PAWS).

In one embodiment, the detoxification agent (anti-addiction agent) is a therapeutically effective amount of one or more opioid antagonist. In one embodiment, the detoxification agent is an opioid agonist, an opioid antagonist, or combinations thereof. In one embodiment, the detoxification agent is a therapeutically effective amount of an opioid agonist and an opioid antagonist.

In one embodiment, the detoxification agent is one or more agents selected from the group consisting of naltrexone, methylnaltrexone, nalmefene, nalmephene, disulfuram, acamprosate, topiramate, risperidone, paliperidone, ondansetron, fluoxetine, sertraline, paroxetine, citalopram, fluvoxamine, venlafaxine and duloxetine.

In certain embodiments, naltrexone is used in combination therapy with one or more other agents for treating an addiction. Such agents include, but are not limited to, analgesics, NSAIDs, antiemetics, antidiarrheals, alpha-2-antagonists, benzodiazepines, anticonvulsants, antidepressants, and insomnia therapeutics. Exemplary agents include, but are not limited to, buprenorphine, naloxone, methadone, levomethadyl acetate, L-alpha acetylmethadol (LAAM), hydroxyzine, diphenoxylate, atropine, chlordiazepoxide, carbamazepine, mianserin, benzodiazepine, phenoziazine, disulfuram, acamprosate, topiramate, ondansetron, sertraline, bupropion, amantadine, amiloride, isradipine, tiagabine, baclofen, propranolol, desipramine, carbamazepine, valproate, lamotrigine, doxepin, fluoxetine, imipramine, moclobemide, nortriptyline, paroxetine, sertraline, tryptophan, venlafaxine, trazodone, quetiapine, zolpidem, zopiclone, zaleplon, gabapentin, naltrexone, paracetamol, metoclopramide, loperamide, clonidine, lofexidine, and diazepam.

In one embodiment, the detoxification agent is one or more agents selected from the group consisting of Clonidine, methocarbamol (Robaxin), pro-banthine, gabapentin, ropinirole, and trazodone.

In certain embodiments in which a subject is provided with both an opioid antagonist and an opioid agonist, the opioid agonist is selected from the group consisting of alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, tramadol, and any combination thereof.

In certain embodiments, naltrexone is used in combination therapy with one or more other anti-epileptic agents selected from the group consisting of carbamazepine (Tegretol), divalproex sodium (Depakote), felbamate (Felbatol), gabapentin (Neurontin), lamotrigine (Lamictal), oxcarbazepine (Trileptal), phenytoin (Dilantin), topiramate (Topamax), and zonisamide (Zonegran)

In certain embodiments, naltrexone is used in combination therapy with one or more other anti-migraine agents selected from the group consisting of serotonin 5HT1d receptor agonists, almotriptan (Axert), frovatriptan (Frova), naratriptan (Amerge), rizatriptan (Rizalt), sumatriptan (Imitrex), zolmitriptan (Zomig), ergot alkaloids dihydroergotamine (DHE), isometheptine/dichlorophenazone (Midrin), caffeine and pizotifen (Sanomigran)

In certain embodiments, naltrexone is used in combination therapy with one or more other sedative-hypnotic agents selected from the group consisting of benzodiazepines, alprazolam (Xanax), clonazepam (Klonopin), clorazepate (Tranxene), diazepam (Valium), flumazenil (Romazicon), antagonist lorazepam (Ativan), midazolam (Versed), triazolam (Halcion), barbiturates/Anesthetics pentobarbital (Nembutal), phenobarbital (Luminal), thiopental (Pentothal), non-depressant anxiolytic and buspirone (BuSpar).

In certain embodiments, naltrexone is used in combination therapy with one or more other pain management agents selected from the group consisting of beta-endorphin, dynorphin, enkephalins, codeine, etorphine, fentanyl (Sublimaze), hydrocodeine, hydromorphone, meperidine (Demerol), methadone (Dolophine), morphine, oxycodone, propoxyphene, buprenorphine, dezocine (Dalgan), nalbuphine (Nubain), pentazocine (Talwain), naloxone (Narcan), acetaminophen (tylenol), and tramadol (ultram).

In certain embodiments, naltrexone is used in combination therapy with one or more other anti-Parkinsonism agents selected from the group consisting of levodopa, carbidopa, bromocriptine (Parlodel), pergolide (Permax), amantadine (Symmetrel), selegiline (Deprenyl), anticholinergic agents, dopamine Agonists, pramipexole (Mirapex), ropinirole (Requip), COMT inhibitors, entacapone (Comtan) and tolcapone (Tasmar).

In certain embodiments, naltrexone is used in combination therapy with one or more other anti-spasticity agents selected from the group consisting of baclofen, (Lioresal), botulinum toxin type A (Botox), carisoprodol (Soma, Rela), chlorphenesin (Maolate), chlorzoxazone (Paraflex), cyclobenzaprine (Flexeril), dantrolene (Dantrium), diazepam (Valium), metaxalone (Skelaxin), methocarbamol (Robaxin), orphenadrine (Norflex), and tizanidine (Zanaflex).

In certain embodiments of the methods of the present invention, the subject is addicted to an addictive agent, or at risk for relapse use of an addictive agent. In particular embodiments, the addictive agent is alcohol, nicotine, marijuana, a marijuana derivative, an opioid agonist, a benzodiazepine, a barbiturate, or a psychostimulant. In certain embodiments, the opioid agonist is selected from the group consisting of: morphine, methadone, fentanyl, sufentanil and heroin. In certain embodiments, the psychostimulant is cocaine, amphetamine, or an amphetamine derivative. In addition, the subject may be addicted to more than one addictive agent, and the pharmaceutical compositions, unit dosage forms, and kits may be useful for treating or preventing addiction or relapse use of more than one addictive agent.

In a related embodiment, the present invention provides a method of treating or preventing an addiction, comprising providing to a subject having an addiction a peroxisome proliferator-activated receptor gamma (PPAR-gamma agonist) and an additional therapeutic agent, wherein each of the PPAR-gamma agonist and the additional therapeutic agent contribute to the effective treatment or prevention of the addiction. In certain embodiments of the methods of treating or preventing addiction of the present invention, the PPAR-gamma agonist is a thiazolidinedione (TZD). In particular embodiments, the TZD is pioglitazone, rosiglitazone, ciglitazone, troglitazone, englitazone, rivoglitazone, or darglitazone. In certain embodiments, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a $5\text{-HT}_{2A/2C}$ antagonist, or a cannabinoid-1 (CB1) receptor antagonist. In particular embodiments, the opioid antagonist is naltrexone or nalmefene. In particular embodiments, the antidepressant is fluoxetine, mirtazapine, or bupropion. In particular embodiments, the antiepileptic is topiramate, levetiracetam, or gabapentin. In one embodiment, the CRF-1 receptor antagonist is antalarmin. In another embodiment, the selective serotonin-3 (5-HT3) antagonist is ondansetron. In particular embodiments, the cannabinoid-1 (CB1) receptor antagonist is rimonabant or tanarabant. In one embodiment, the mixed opioid agonist/antagonist is buprenorphine.

In other embodiments of the present invention, the subject is addicted to an addictive or compulsive behavior or at risk for relapse practice of an addictive or compulsive behavior. In particular embodiments, the addictive or compulsive behavior is pathological gambling, pathological overeating, pathological use of electronic devices, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking. In addition, the subject may be addicted to more than one addictive or compulsive behavior, and the pharmaceutical compositions, unit dosage forms, and kits may be useful for treating or preventing addiction or relapse use of more than one addictive or compulsive behavior.

In particular embodiments of any of the methods of the present invention, the addictive agent is alcohol and the additional therapeutic agent is an opioid antagonist or a mixed opioid antagonist/partial agonist. In one embodiment, the opioid antagonist is naltrexone. In another embodiment, the mixed opioid partial agonist/antagonist is buprenorphine.

In other particular embodiments of any of the methods of the present invention, the addictive agent is nicotine and the additional therapeutic agent is an antidepressant. In one embodiment, the antidepressant is bupropion.

In further particular embodiments of any of the methods of the present invention, the addictive agent is a psychostimulant and the additional therapeutic agent is an antidepressant. In one embodiment, the antidepressant is bupropion.

In certain embodiments of pharmaceutical compositions of the present invention comprises one or more additional therapeutic. In certain embodiments the one or more additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT2A/2C antagonist, and a cannabinoid-1 (CB1) receptor antagonist. In one embodiment, the opioid antagonist is naltrexone or nalmefene. In one embodiment, the antidepressant is fluoxetine, mirtazapine, or bupropion. In one embodiment, the antiepileptic is selected from the group consisting of: topiramate, levetiracetam, and gabapentin. In one embodiment, the CRF-1 receptor antagonist is antalarmin. In one embodiment, the selective serotonin-3 (5-HT3) antagonist is ondansetron. In one embodiment, the cannabinoid-1 (CB1) receptor antagonist is rimonabant or tanarabant. In one embodiment, the mixed opioid agonist/antagonist is buprenorphine.

An opioid antagonist acts on one or more opioid receptors. At least three types of opioid receptors, mu, kappa, and delta opioid receptors, have been reported, and opioid antagonists are generally classified by their effects on the opioid receptors. Opioid antagonists may antagonize central receptors, peripheral receptors or both. Naloxone and naltrexone are commonly used opioid antagonist drugs that are competitive that bind to the opioid receptors with higher affinity than agonists, but that do not activate the receptors. This effectively blocks the receptor, preventing the body from responding to opiates and endorphins.

Many opioid antagonists are not pure antagonists but also produce some weak opioid partial agonist effects and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists.

Naloxone is one example of an opioid antagonist that has no partial agonist effects. Instead, it is a weak inverse agonist at mu opioid receptors and is used for treating opioid overdose.

Specific examples of opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxone, naloxonazine, naltrendol, naltrexone, naltrindole, oxilorphan, and pentazocine.

The term addiction is used to describe a recurring compulsion by an individual to engage in some specific activity, despite harmful consequences to the individual's health, mental state or social life. The term is often reserved for drug addictions, but it is sometimes applied to other compulsions, such as problem gambling, and compulsive overeating. Factors that have been suggested as causes of addiction include genetic, biological/pharmacological and social factors. The medical community now makes a careful theoretical distinction between physical or physiological dependence (characterized by symptoms of withdrawal) and psychological dependence (sometimes referred to simply as addiction). Addiction is now narrowly defined as "uncontrolled, compulsive use." If there is no harm being suffered by, or damage done to, the patient or another party, then clinically it may be considered compulsive, but to the definition of some it is not categorized as "addiction". In practice, the two kinds of addiction (physiological dependence and psychological dependence) are not always easy to distinguish. Addictions often have both physical and psychological components. Physical dependence (or drug dependence) refers to a state resulting from habitual use of a drug, where negative physical withdrawal symptoms result from abrupt discontinuation. Examples of addictive agents for which a user may develop a physical dependence include nicotine, opioids, barbiturates, benzodiazepines, alcohol, i.e., ethyl alcohol, GHB, and methaqualone.

Physical dependence (or drug dependence) refers to a state resulting from habitual use of a drug, where negative physical withdrawal symptoms result from abrupt discontinuation. Examples of addictive agents for which a user may develop a physical dependence include nicotine, opioids, barbiturates, benzodiazepines, alcohol, i.e., ethyl alcohol, GHB, and methaqualone.

Commonly abused stimulants such as cocaine or amphetamine class drugs are not believed to cause significant physical dependence. However, their potential for extreme physiological addiction can compel the user to consume amounts which become physically damaging, but life-threatening withdrawal effects have not been observed.

As used herein, addictive agents includes any and all agents to which a subject can become addicted, either physically or psychologically, or both. As noted above, addiction includes addiction to chemical entities, such as drugs, e.g., ethyl alcohol, nicotine, or cocaine, as well as addiction to other behaviors, e.g., pathological gambling, pathological overeating, pathological use of electronic devices, e.g., BlackBerry, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking.

Addictive agents include addictive recreational drugs, as well as addictive medications. Examples of addictive agents include, but are not limited to, alcohol, e.g., ethyl alcohol, gamma hydroxybutyrate (GHB), caffeine, nicotine, cannabis (marijuana) and cannabis derivatives, opiates and other morphine-like opioid agonists such as heroin, phencyclidine and phencyclidine-like compounds, sedative hypnotics such as benzodiazepines, methaqualone, mecloqualone, etaqualone and barbiturates and psychostimulants such as cocaine, amphetamines and amphetamine-related drugs such as dextroamphetamine and methylamphetamine.

In one or more embodiments, the method comprises at least one sedative selected from the group consisting of benzodiazepines and Z-drugs. Common benzodiazepines include Xanax (alprazolam), Librium (chlordiazepoxide), Valium (diazepam), and Ativan (lorazepam). Common Z-drugs include Ambien (zolpidem), Lunesta (eszopiclone), and Sonata (zaleplon).

Other examples include LSD, psilocybin, extasy and other hallucinogens. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxycontin, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed μ-agonists/antagonists, and the like.

In certain embodiments, a subject may be addicted to an opioid agonist. The terms "opioid agonist," "opioid" and "opiate" are used interchangably herein and are used to designate a group of drugs that are, to varying degrees, opium-or morphine-like in their properties. Their main use is for pain relief. These agents work by binding to opioid receptors, which are found principally in the central nervous system and the gastrointestinal tract. Opiates are also addictive agents. Opiates include, e.g., alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, and tramadol. Naturally occurring opiates include, e.g., codeine, morphine, noscapine, papaverine, and thebaine. Semi-synthetic opioids include, e.g., diacetylmorphine, hydrocodone, hydromorphone, levorphanol, metapon, nalorphine, naloxone, naltrexone, oxycodone, oxymorphone, and tramadol. Synthetic opioids include, e.g., ethoheptazine, fentanyl, levorphanol, meperidine, methadone, phenazocine, propoxyphene and sufentanil. Three broad classifications of opiates are phenanthrenes, phenylheptylamines, and phenylpiperidines. Examples of phenanthrenes include codeine, etorpine, hydrocodone, hydromorphone, morphine, oxycodone, and oxymorphone. Examples of phenylheptylamines include dimeheptanol, dimenoxadol, dipipanone, isomethadone, methadone, methadyl acetate, and propoxyphene. Examples of phenylpiperidines include alfentanyl, alphaprodine, beta-promedol, carfentanil, fentanyl, lofentanil, meperidine, properidine, and sufentanil.

The present invention provides for systems and methods for reducing or eliminating the physical signs and symptoms of withdrawal from addiction or substance abuse e.g., opiates, narcotics, alcohol, amphetamines, methamphetamines or any substance that is known to cause withdrawal symptoms.

Reducing the subjective and objective scores of C.O.W.S. or any other outcomes or assessment tool with any auricular or peri-auricular electro-acupuncture or neurostimulation device, with the intention of stabilizing the patient to a point that any drug or alcohol screen can be found "negative" (clean), with the intention of getting the patient to a medication like naltrexone/naloxone (Vivitrol) or any other similar medication.

The use of medication assisted detoxification along with the BRIDGE device or any similar device to provide humane detoxification to avoid addicting medications.

That this protocol will reduce the normal withdrawal times from 10-21 days, to 2-11 days.

That this protocol offers the first ever opportunity for a patient to choose a treatment that will allow them to get off of addicting medications, alcohol, heroin or any other addicting substance, without suffering the intense and painful signs and symptoms of withdrawal.

The present invention provides accelerated detoxification methods for the treatment of a substance abuse-related condition in a subject. In another embodiment, present invention provides accelerated detoxification methods for the treatment of drug, alcohol or behavioral addiction.

Thus, the present invention includes methods of treating or preventing an addiction, comprising providing one or more opioid agonist, opioid antagonist or combination thereof to a subject having an addiction or at risk for developing an addiction. In various embodiments, the subject is addicted to an addictive agent or behavior, including, but not limited to, any of the addictive agents and behaviors described herein. The subject may be physically or physiologically dependent on the substance or behavior; the subject may be psychologically dependent; or the subject may be both physically and psychologically dependent. The subject may be addicted to one or more than one addictive agent or behavior.

As used herein, unless the context makes clear otherwise, "treat," and similar word such as "treatment," "treating" etc., is an approach for obtaining beneficial or desired results, including and preferably clinical results. Treatment can involve optionally either the reducing or amelioration of a disease or condition, (e.g., addiction, relapse use, withdrawal), or the delaying of the progression of the disease or condition (e.g., addiction relapse use, withdrawal). The subject may be any animal, including a mammal, and, particularly, a human.

As used herein, unless the context makes clear otherwise, "prevent," and similar word such as "prevention," "preventing" etc., is an approach for preventing the onset or recurrence of a disease or condition, (e.g., addiction, relapse use, withdrawal) or preventing the occurrence or recurrence of the symptoms of a disease or condition, or optionally an approach for delaying the onset or recurrence of a disease or condition or delaying the occurrence or recurrence of the symptoms of a disease or condition. Preventing also includes inhibiting the onset or recurrence of a disease or condition, or one or more symptoms thereof, and reducing the likelihood of onset or recurrence of a disease or condition, or one or more symptoms thereof.

Generally, a subject is provided with an effective amount of an opioid agonist, opioid antagonist or combination thereof. As used herein, an "effective amount" or a "therapeutically effective amount" of a substance, e.g., an opioid agonist, opioid antagonist or combination thereof, is that amount sufficient to affect a desired biological or psychological effect, such as beneficial results, including clinical results. For example, in the context of treating addiction using the methods of the present invention, an effective amount of an opioid agonist, opioid antagonist or combination thereof is that amount sufficient to cause the subject to reduce or discontinue use of an addictive agent.

The terms "substance abuse," "substance-dependence," "substance addiction," "drug abuse," "drug dependence," and "drug addiction," as used herein, may be used interchangeably and refer to the overindulgence in and dependence on an opiate, a stimulant, a depressant, and/or other chemical substance, leading to effects or conditions that are detrimental to the user's physical or mental health, and/or the welfare of others. Similarly, a substance abuse, dependence, or addiction-related condition may include, without limitation, any physical, mental, physiological, pathological, psychological, psychiatric, and/or clinical conditions related to the use or abstinence from use of a chemical substance, including any withdrawal syndrome resulting from discontinuation of use of substances, such as, opioids or opiates, either natural or synthetic.

In one aspect of the invention, the subject is first determined or diagnosed to have an addiction, or to be at risk of developing an addiction, by diagnostic testing, observation or analysis by a medical care provider. An effective amount of an opioid antagonist, or an effective amount of an opioid antagonist and one additional therapeutic agent, are then provided to the subject for treatment or prevention of the addiction. In another aspect of the invention, the subject is first determined or diagnosed to have an addiction, or to be at risk of developing an addiction, by diagnostic testing, observation or analysis by a medical care provider, but the subject has not been diagnosed or determined to have diabetes or other insulin disorder. An effective amount of an opioid antagonist, or an effective amount of an opioid antagonist and one additional therapeutic agent, are then provided to the subject for treatment or prevention of the addiction. The dosage of the opioid antagonist, or the opioid antagonist and the one additional therapeutic agent, may be specifically determined by the medical practitioner for treatment or prevention of the addiction rather than for any other disorder or disease.

Typical opioid withdrawal syndrome may include, without limitation, sweating, restlessness, bone and/or joint aches, muscle spasms/twitching, runny nose or tearing, gastrointestinal conditions (e.g., without limitation, stomach cramps, nausea, vomiting, loose stool, and diarrhea), tremor, yawning, anxiety, and gooseflesh skin. As used herein, the term "substance" may include any natural, synthetic, opiate, opioid, or narcotic compounds or compositions (including, without limitation, opioid, opioid derivatives, opioid agonists, and opioid antagonists). Examples of such substances include, without limitation, opium, morphine, heroin, pethidine, methadone, buprenorphine, butorphanol, codeine, fentanyl, hydrocodone, hydromorphone, levorphanol, meperidine, oxycodone, pentazocine, propoxyphene, and tramadol.

As used herein, the phrase "treatment of a substance abuse-related condition" includes efforts, actions, conducts, and/or procedures to ameliorate, reduce, minimize, eliminate, or prevent any physical, mental, physiological, pathological, psychological, psychiatric, and/or clinical conditions or impairments related to or resulting from a substance abuse, addiction, dependence, or the withdrawal therefrom. For example, without limitation, clinical impairments or symptoms of a substance abuse-related condition may be ameliorated or minimized by diminishing any pain or discomfort suffered by the subject; by inhibiting, reducing, or preventing the development of a substance abuse-related condition; or by limiting, suspending, terminating, or otherwise controlling a substance abuse-related condition.

As used herein, the term "detoxifying amount of an opioid antagonist" includes an effective amount of an opioid antagonist, which may substantially saturate, bind to, or block an effective number of the opioid receptors in a subject. The terms "substantially saturate" and "substantially block" an effective number of opioid receptors include about 75%, about 80%, about 85%, about 90%, about 95%, or higher, saturation or blockage of the opioid receptors in a subject.

In one aspect, a detoxifying amount comprises up to about 2000 micrograms of naloxone, which may be given, for example, intravenously or intramuscularly, to a subject over a period of time, such as, within 4-6 hours. Such a detoxifying amount of naloxone may be followed by about 0.5 mg to about 10 mg bolus administration of an antagonist such as naltrexone, or about 1 mg to about 8 mg, or about 2 mg to about 6 mg, or about 3 mg to about 5 mg, or about 1 mg, 2 mg, 3 mg, 4 mg, 5 mg, 6 mg, 7 mg 8 mg, 9 mg or 10 mg of an antagonist. Not wishing to be bound by any particular theory, it is currently thought that providing a bolus administration of an opiate antagonist provides antagonist support in the administration of an implant of an opiate antagonist, and may be additional support for the detoxifying amount of antagonist provided.

The treatment method days, up to but not including the summit day wherein a detoxifying amount of an opiate antagonist is provided, may be about 1 to about 15 days, or about 2 to about 8 days. On a summit day, a detoxifying amount such as 2,000 ug of an opiate antagonist such as naltrexone or naloxone may be administered intravenously, and optionally followed by a bolus administration of an opiate antagonist. The summit day may be followed by continuous administration of an opiate antagonist, such as by providing a sustained release delivery form of an opiate antagonist, such as naltrexone.

For example, an 8 day treatment method may be appropriate for subjects dependent on methadone, buprenorphine, suboxone, or other long-acting opiates because of the long half-life of those drugs and the severity of the withdrawal symptoms if the detoxifying treatment is performed too rapidly. In one aspect, the subject may use as small amounts of opioids (e.g., tramadol) as possible and use as large amounts of micro-dose opioid antagonists (e.g., naltrexone) as possible, in part to control withdrawal symptoms, during the treatment period up to the summit day.

To aid in preventing relapse following the detoxifying treatment, an opioid antagonist (e.g., naltrexone or Vivitrol) may be administered to the subject for an extended period of time, such as, for about 1 to about 24 months, or for about 12 months. The opioid antagonist may be given to the subject using any suitable method, such as, but not limited to, orally, I.M. (intramuscular injection) or in an implant form. In one aspect, the opioid antagonist, such as, naltrexone, may be given to the subject in the form of a controlled/sustained release pharmaceutical composition. For example, a sustained release pellet containing naltrexone may be implanted under the subject's skin, such as, without limitation, in the fatty tissue of the lower abdomen. The controlled release pharmaceutical composition may release an effective amount of the opioid antagonists (e.g., naltrexone) over a period of more than about 6 to about 8 weeks or more than about 8 to about 10 weeks, up to about 12 or about 24 months. Controlled release pharmaceutical compositions comprising opioid antagonist (e.g., naltrexone) and methods for delivering an effective amount of opioid antagonist are known in the art.

The compositions of the present invention may be administered to a subject independently, or together with other pharmaceutical compositions. It may also be administered to a subject together with food or a beverage.

A pharmaceutical composition of the present invention may be administered to a subject by known procedures, including, without limitation, oral administration, parenteral administration, transdermal administration, nasal administration, and by way of catheter. For example, the pharmaceutical composition may be administered orally, parenterally, by epifascial, intracapsular, intracranial, intracutaneous, intrathecal, intranasal, intramuscular, intraorbital, intraperitoneal, intraspinal, intrasternal, intravascular, intravenous, parenchymatous, subcutaneous, or sublingual administration. The pharmaceutical composition may be provided in an amount effective to treat a pathological or psychiatric condition in a subject to whom the composition is administered. As used herein, the phrase "effective to treat a disorder" means effective to eliminate, ameliorate, reduce, minimize, or prevent the clinical impairment or symptoms associated with the disorder.

For oral administration, the pharmaceutical composition of the present invention may be presented as capsules, tablets, powders, granules, or as a suspension, among others. The formulation may have conventional additives, such as, but not limited to, lactose, mannitol, corn starch, or potato starch. The formulation also may be presented with binders, such as, crystalline cellulose, cellulose derivatives, acacia, corn starch, and gelatins, among others. Additionally, the formulation may be presented with disintegrators, such as, but not limited to, corn starch, potato starch, and sodium carboxymethylcellulose. The formulation also may be presented with dibasic calcium phosphate anhydrous or sodium starch glycolate. Moreover, the formulation may be presented with lubricants, such as talc and magnesium stearate.

For parenteral administration (i.e., administration by injection through a route other than the alimentary canal), the pharmaceutical composition of the present invention may be combined with a sterile aqueous solution that may be isotonic with the blood of the subject. Such a formulation may be prepared by dissolving the pharmaceutical composition of the present invention in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, and sublingual.

For transdermal administration, the pharmaceutical composition of the present invention may be combined with skin penetration enhancers, such as propylene glycol, polyethylene glycol, isopropanol, ethanol, oleic acid, N-methylpyrrolidone, and the like, which increase the permeability of the skin to the pharmaceutical composition, and permit the pharmaceutical composition to penetrate through the skin and into the bloodstream. The pharmaceutical composition of the present invention may be further combined with a polymeric substance, such as ethylcellulose, methylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch.

The pharmaceutical composition of the present invention may comprise a pharmacological effective amount of a compound and a pharmaceutically-acceptable carrier. The pharmaceutically-acceptable carrier may be "acceptable" in the sense of being compatible with the other ingredients of the composition, and not deleterious to the recipient thereof. The pharmaceutically-acceptable carrier employed herein may be selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

In one embodiment, the auricular or peri-auricular electro-acupuncture or neurostimulation device comprises:
  (a) a stimulator comprising (i) a generator for generating electrical stimulation pulses with defined stimulation parameters, (ii) a voltage supply for supplying the generator with electrical energy and (iii) a control device for generating stimulation pulses from the generator having a defined current voltage or current amplitude, a defined duration, a defined repetition frequency and a defined duty cycle;
  (b) at least one therapy electrode connected to the stimulator for providing stimulation pulses to an area to be stimulated; and
  (c) at least one reference electrode connected to the stimulator for providing a ground connection for the stimulator
  (d) wherein the at least one therapy electrode comprises an array of at least two (2) needle electrodes for insertion into the skin surface of an area to be stimulated;
  (e) wherein the needle electrode array is designed for auricular peripheral or cranial nerve field stimulation.

A stimulation device, wherein the electrical signal generator is configured to generate electrical stimulation pulses having a repetition frequency of 0.5 to 300 Hz and a duty cycle of 5-100%, preferably 98-100% and wherein the stimulation pulses are generated at a constant current amplitude.

A stimulation device, wherein the electrical signal generator is configured to generate electrical stimulation pulses having a frequency modulating from 0 to 300 Hz. A stimulation device, wherein the electrical signal generator is configured to generate electrical stimulation pulses having a frequency modulating from 1 Hz, 3 Hz, 7 Hz, 10 Hz, repeating. A stimulation device, wherein the voltage output to the therapy electrodes is in the range of about 0.001 volts to 6 volts.

A stimulation device, wherein the electronic aspects of the electrical stimulation device are implemented by means of an analogue circuit, a digital circuit or a computer arrangement with a processor instructed by a suitable computer program, or any combination thereof. A stimulation device, wherein the stimulator further comprises a program for performing stimulation wherein the program is resident in a memory and executed by a microprocessor to control the stimulator.

A stimulation device, wherein the control device is coupled to operating elements for changing the stimulation parameters. A stimulation device, wherein the control device is coupled to operating elements comprising controls for the ability to adjust the voltage output to the therapy electrodes by manipulation of one or more parameters selected from the group consisting of pulse frequency, pulse width, provision of sequential pulses, output of more than one pulse at a time and combinations thereof.

A stimulation device, further comprising a memory for recording the stimulation parameters as a function of time.

A stimulation device, wherein the control device comprises electrically erasable programmable read-only memory (EEPROM) configured to provide electrical pulses for at least 2 hours, follow by at least 30 seconds of a low power delay cycle with no pulse output.

Aspects of the present disclosure are directed toward auricular nerve stimulation at terminals in one and/or both ear lobes, and based on events that are simultaneous, synchronous, in alternating sequences and/or with different off times, and to providing systems, apparatuses, and methods for application of stimulation for reproducible stimulation of the auricular nerve or nerves with minimal operator dependence.

Device, systems, methods and kits can be useful for auricular stimulation. One such device relates to auricular stimulation. The device includes one or two earpieces having an electrode arrangement configured and arranged to deliver a series of electrical stimulation signals to one or two auricular locations.

Certain embodiments of the present disclosure are directed toward an auricular stimulation device that has an earpiece having an electrode and configured and arranged to deliver a series of electrical stimulation signals to a first auricular location of a particular individual based upon anatomical measurements from the particular individual. A pulse-generator circuit is configured and arranged to generate the series of electrical stimulation signals, and to deliver the electrical stimulation signals to the electrode.

Various embodiments of the present disclosure are directed toward a method of auricular stimulation. A stimulation location is determined from anatomic points of an ear of a subject. An earpiece, having a stimulation electrode, is positioned so as to locate the stimulation electrode in a location corresponding to the stimulation location. A series of electrical stimulation signals are delivered to the stimulation electrode according to a stimulation profile.

Additional Embodiments

The methods of the present invention make use of an electrical stimulation device including a stimulator described for treating symptoms of drug withdrawal, specifically withdrawal from opioids.

A protocol has been described to make use of device along with medications designed to promote comfort for an approximately 5-day period with the goal to get onto opioid antagonist therapy with a long acting naltrexone product. Long acting naltrexone currently comes in the form of a monthly depot injection, Vivitrol, and various naltrexone implants.

Published study describes 85% of opioid withdrawal symptoms being controlled within 30 minutes. Residual symptoms are controlled using comfort medications described in protocol. (Miranda A, Babygirija R. Neurostimulation with IBStim attenuates amygdala neurons and prevents post-inflammatory visceral and somatic hyperalgesia in rats. World Congress of pediatric gastroenterology, hepatology and nutrition).

Mechanism of action of device is most likely from autonomic regulation from stimulating the Vagus Nerve promoting Parasympathetic activity. Imaging study in rats shows 65% reduction in neuronal firing of the Amygdala, the area of the brain which controls emotional tone which includes fear, terror, and anxiety. (Journal of Addiction Medicine. Neuromodulation with BRIDGE is Associated with Reduction in Signs and Symptoms of Opioid Withdrawal-A Retrospective, Multisite Study).

Other possible mechanisms of action include disruption of ascending and descending pain tracks of the dorsal column, stimulation of Trigeminal nerve causing release of pain modulating neurochemicals of endorphin from para-aqueductal grey and serotonin from raphe nucleus.

Comfort medication are utilized within this period of detoxification because of presence of residual symptoms. Possible explanation of incomplete resolution of withdrawal symptoms can be explained by nerve attenuation during this period. Nerve attenuation can be described as the reduction of the amplitude of a signal, electric current, or action potential of a nerve.

In one embodiment, the present invention includes a method of treating or preventing an addiction, comprising determining that a subject has or is at risk of developing an addiction, and providing to the subject one or more non-narcotic detox medications used in combination with one or more auricular or peri-auricular electro-acupuncture or neurostimulation device for a time effective for the treatment or prevention of the addiction.

In a related embodiment, the present invention provides a method of treating or preventing an addiction, comprising providing to a subject having an addiction one or more non-narcotic detox medications used in combination with one or more auricular or peri-auricular electro-acupuncture or neurostimulation device and an additional therapeutic agent, wherein each of the one or more non-narcotic detox medications and the additional therapeutic agent contribute to the effective treatment or prevention of the addiction.

In one embodiment, the invention providers for a method of treating or preventing an addiction, comprising providing to a subject having an addiction one or more non-narcotic detox medications used in combination with one or more auricular or peri-auricular electro-acupuncture or neurostimulation device wherein the left side of the body is implanted first to reduce chance of any cardiac effects. Without wishing to be bound by theory, it is believed that the right side has some projections to the heart and can cause feinting. In another embodiment, the left side of the body is implanted only without implantation on the right side to reduce chance of any cardiac effects. In another embodiment, the right side can be used if left sided cannot be done.

In one embodiment, the invention providers for a method of treating or preventing an addiction, comprising right sided vagus nerve stimulation. The vagus nerve, also called X cranial nerve or 10th cranial nerve, is the longest and most complex of the cranial nerves. The vagus nerve runs from the brain through the face and thorax to the abdomen. It is a mixed nerve that contains parasympathetic fibres. One or more auricular or peri-auricular electro-acupuncture or neurostimulation devices can be used to stimulate the vagus nerve on and around the neck and ear.

In one embodiment, the invention providers for a method of treating or preventing an addiction, comprising bilateral implantation using two devices that are identically preprogrammed for an amount of time alternating on/off stimulation on each ear for the period of the detoxification. This is to reduce nerve attenuation and need for complicated comfort medication regimen.

In one embodiment, the invention providers for a method of treating or preventing an addiction, comprising using the left ear first for stimulation before the right. In one embodiment, the left ear is the preferred site as the right sided auricular branches of the vagus nerve innervates the sinoatrial node of the heart and influences the heart rate. R-VNS seems to be an effective and alternative therapy in selected patients responding to L-VNS where a left-sided reimplantation is not possible. (Epilepsy Res. 2008 December; 82(2-3):232-4. doi: 10.1016/j.eplepsyres.2008.08.003. Epub 2008 Sep. 18.)

Nerve Attenuation

Because of possible nerve attenuation during this period, an approach has been described to take advantage of bilateral auricular and facial branches of Cranial Nerves.

Cardiac slowing in response to a standard electrical stimulus applied to the vagus (1-2 Hz for 10 s) was potentiated after a 2-min high frequency stimulation (10 Hz). This potentiation of cardiac vagal action was abolished after a 1-hour period of repetitive vagal stimulation. (Cardiac vagal effects in the toad are attenuated by repetitive vagal stimulation. Neuropeptides. 1993 September; 25 (3): 193-8.)

Bilateral Approach

In one embodiment, the protocol requires two pre-programmed devices implanted bilaterally. The first device would be implanted and be programmed with alternating times of stimulation. Once the first device is programmed to stop stimulation, to prevent nerve attenuation, a second device would be installed in the opposite ear. The second device would take over stimulation for the same period while the first device is off.

Since nerve attenuation can be seen between 1-6 hours of placement of the device, it is suggested that both devices be programmed with identical alternating stimulations for 1-6 hours. In one embodiment, a schedule with 2-3 hours on/off schedule is used.

For example, a person presents in moderate to severe opioid withdrawal. Device #1 is installed, and patient is either supervised in the clinic for the next 2 hours or asked to come back within 2 hours to prepare for installation of device #2. It is important to implant device #2 when device #1 is programmed to be off. After 2 hours the patient presents again to the clinic and device #2 is installed in the opposite ear. Device #1 will not be taken off. Both devices will be worn for the total of 120 hours (5 days).

In one embodiment, both devices are identically preprogrammed, in this example, for 2 hours of alternating electrical stimulation. This approach can minimize nerve attenuation and use of comfort medications. This can then reduce the total drug amounts needed for treatment.

Example Devices that can be Used in the Present Methods

The present invention relates to methods and systems for treatment of addiction using electrode placement for auricular peripheral nerve field stimulation (PNFS) using a method of anatomical visualization and percutaneous implantation of an electrode complex(es) designed as a needle array.

In one embodiment, the invention providers for a single use device that is physician applied for ambulatory, continuous, home based therapy. In one embodiment, the stimulator is percutaneously implanted into the cranial and/or peripheral nerves and corresponding neural vascular bundles of the auricular and periauricular areas as ascertained by the method of evaluating and implanting of the electrode/needle array provided in the present invention. This includes transillumination of the auricular and periauricular tissues and surrounding neurovascular anatomy. The auricular peripheral nerve stimulator system allows for continuous, intermittent neural stimulation.

In one embodiment, the auricular peripheral nerve stimulator system is a battery-operated, single-use device that has a preprogrammed frequency, pulse and duration for the stimulation of selected cranial and/or peripheral nerves and corresponding neural vascular bundles of auricular and periauricular areas. In one embodiment, the device power supply connects via three or more electrical conduit wires, sheathed in electrically insulating material, to one or more therapy electrode arrays comprised of multiple needles each and one reference electrode.

In another embodiment, the device comprises two or more needle arrays comprised of multiple needles each. In another embodiment, the device comprises three or more needle arrays comprised of multiple needles each. In another embodiment, the device comprises four or more needle arrays comprised of multiple needles each. In another embodiment, the needle arrays are comprised of two or more needles each. In another embodiment, the needle arrays are comprised of three or more needles each. In another embodiment, the needle arrays are comprised of four or more needles each. In another embodiment, the needle arrays are comprised of five or more needles each. In another embodiment, the needle arrays are comprised of six or more needles each.

Figures 1A, 1B:
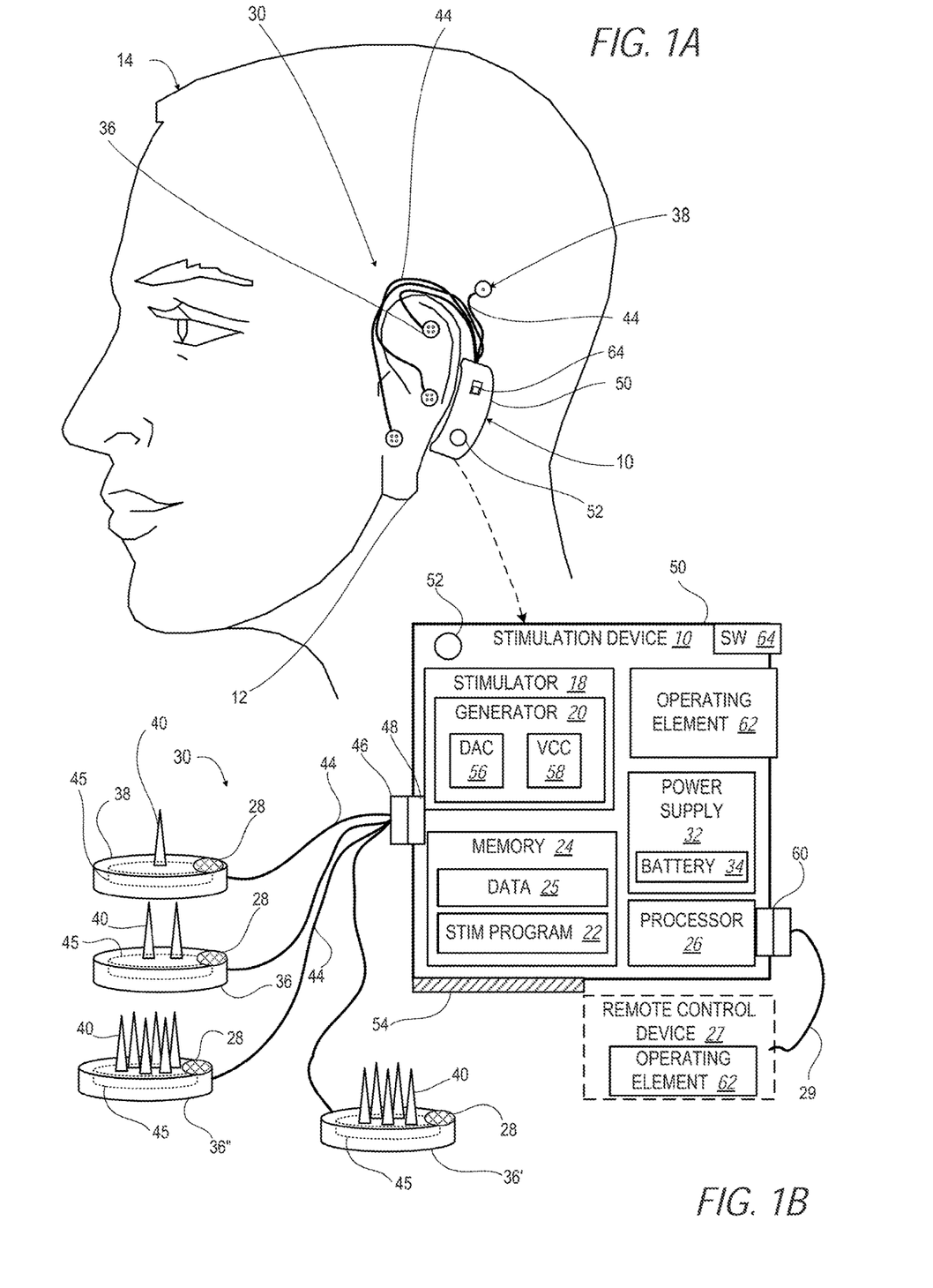
FIG. 1A is a side view of a head of a human being with an electrical stimulation device in an auricular application, according to one embodiment.
FIG. 1B is a block diagram of the electrical stimulation device of FIG. 1B, according to one embodiment.

Turning to the drawings, FIGS. 1A-1B depict an electrical stimulation device 10 for, in particular, an electrical acupuncture therapy in the region of an ear 12 of a human being 14. The stimulation device 10 includes a stimulator 18 containing a generator 20 for generating stimulation pulses with defined stimulation parameters, i.e. a defined voltage or a defined current, a defined duration, a defined repetition frequency and a defined duty cycle etc. In one embodiment, the electrical stimulation device 10 comprises an electrical signal generator 20 configured to generate electrical stimulation pulses having a repetition frequency of 0.5 to 100 Hz, preferably 1-10 Hz, and a duty cycle of 10 to 90%, preferably 40-60%. In one embodiment, the stimulation pulses are generated at a constant current amplitude.

With particular reference to FIG. 1B, electronic aspects of the electrical stimulation device 10 may be implemented by means of an analogue circuit, a digital circuit or a computer arrangement with a processor instructed by a suitable computer program, or any combination thereof. In one embodiment, a program 22 for performing stimulation is resident in memory 24 and executed by a microprocessor 26 to control the stimulator 18. The memory 24 may be implemented as several memory units of different types (RAM, ROM, etc.). The memory 24 stores instructions of a program 22 to allow a microprocessor 26 to perform one or more functions. Optionally, memory 24 stores a number of detected parameter values as obtained from detection devices 28, such as incorporated in an electrode needle array 30. The memory 24 may be any suitable memory 24 for storing a predetermined function such as a computer readable memory 24. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. For example, the function may relate the absence of certain parameter values below a certain threshold value to a certain time frame. Such a function may be determined to detect the absence of breathing during a certain time period e.g. 1 second and longer, 2 seconds and longer or 5 seconds and longer.

Based on the program 22 as stored in the memory 24, the microprocessor 26 is able to process the number of detected parameter values as obtained from the detection device in said function. For this, the detected parameter values are loaded into the microprocessor 26 either directly from the detection devices 28 or alternatively from the memory 24 into which the detected parameter values were previously loaded. The function is loaded in the microprocessor 26 from the memory 24 or in an alternative embodiment the predetermined function may be embedded in said microprocessor 26. In the latter embodiment at least one memory 24 is (partially) integrated in the microprocessor 26. In one embodiment, the memory 24 records the stimulation parameters as a function of time as data 25 to enable the performance of a quality control check or check of the proper operation by a remote control device 27 that is periodically or permanently in communication with the stimulation device 10 via wireless or wired connection 29.

The detection device 28 may be any suitable device for detecting a number of parameter values. In the present specification, a "number" shall mean one or more unless explicitly stated otherwise. Parameters suitable for determining whether a subject is in need of resuscitation include but are not limited to parameters corresponding to muscle activity, parameters corresponding to breathing, or parameters corresponding to cerebral activity, such as electrical activity of neural cells including brain cells, or electrical activity recorded from the ear or any other suitable point on the body of a human being 14. Other sensors may be applied as well, like a sensor to measure body temperature, a sensor to measure pressure, and a sound sensor, like a microphone.

A power supply 32 is provided in order to supply the components of the stimulator 18 with electrical energy. In one embodiment, the power supply 32 is formed by a suitable battery 34 or an accumulator. The electrical pulses generated in the generator 20 of the stimulator 18 are delivered via at least one needle electrode array 30 comprising at least two therapy electrode arrays 36 and at least one ground or reference electrode 38.

Each therapy electrode 36 has two or more needle electrodes 40, which in an exemplary embodiment is four (4) in number. In one embodiment, the number of therapy electrodes 36 is selected from the group consisting of 2, 3, 4, 5, 6, 7, 8, 9, 10, or more. In another embodiment, the number of needle electrodes 40 per therapy electrode 36 is selected from the group consisting of 2, 3, 4, 5, 6, 7, 8, 9, 10, or more. In one embodiment, the number of needle electrodes 40 per therapy electrode 36 is 2-10. In one embodiment, the number of needle electrodes 40 per therapy electrode 36 is 3-9. In one embodiment, the number of needle electrodes 40 per therapy electrode 36 is 4-8. As seen in FIG. 1B, the array may include one or more therapy electrode 36' and 36", alone or in combination, with five (5) and six (6) needle electrodes 40, respectively.

The present invention has shown that the use of therapy electrode 36 having a plurality of two or more needle electrodes 40—and preferably 3 or more and more preferably 4 or more—provides for the unexpected result of a synergistic filed effect and not merely an additive electrical stimulation for pain reduction.

Each reference electrode 38 includes at least at least one needle electrode 40. The therapy electrodes 36 and reference electrode 38 are inserted into the skin surface in the area to be stimulated. The reference electrode 38 provides a ground connection for electronic circuit located within the stimulator 18.

In one embodiment, the needle electrodes are made of an electrically conductive material, in particular a metal such as titanium, stainless steel or the like. In addition to metals, conductive synthetics are also conceivable for the production of the needle electrodes.

In one embodiment, the at least two needle electrodes 40 of the therapy electrode 36 are arranged in a common electrode housing 42 with a detection device 28 and connected to the stimulator 18 by an appropriate line 44. A circuit board 45 (FIG. 1B) on which the one or more needle electrodes 40 are mounted is arranged in the common electrode housing 42. The therapy electrodes 36 can, for instance, be simply connected to the circuit board 45 by a conductive adhesive. The line 44 is likewise connected to the circuit board 45, either by a solder joint or by a screw connection, the conductive tracks of the circuit board 45 safeguarding the electrical connection to the therapy electrodes 36. The arrangement of each therapy electrode 36 in a common electrode housing 42 provides for a defined distance between the individual needle electrodes 40. The line 44 for connecting the therapy electrodes 36 to the stimulator 18 can be fixedly, i.e. inseparably, or even detachably configured. Each line 44 can be fixedly connected respectively to the corresponding therapy electrode 36 or reference electrode 38. Each line 44 can also be fixedly connected to the stimulator 18. In the illustrative embodiment, each line 44 terminates at a plug 46 that is physically and electrically connected to a socket 48 mounted on an electronic housing 50 that contains the stimulator 18.

In order to attach the electronic housing 50 to the skin surface, a fastening element 54 (FIG. 1B), such as an adhesive element, may be provided. Besides the adhesive element, other fastening methods, e.g. via magnets, elastic bands or the like can be used. The fastening element can be integrated in the electrode housing. For example, the electronic housing 50 can adhesively mount behind the ear 12 of the human being 14 (FIG. 1A). The electronic housing 50, which may be made of a synthetic material and is preferably designed to be water-proof. The components depicted in FIG. 1A can be arranged in a preferably sterile package (not illustrated) so as to prevent any contamination of the needle electrode array 30.

In another embodiment, the auricular peripheral nerve stimulator system is a battery-operated, single-use device that has a pre-programmed frequency, pulse, and duration for the stimulation of selected cranial and/or peripheral nerves and corresponding neural vascular bundles of auricular and periauricular areas.

In another embodiment, the auricular peripheral nerve stimulator is a single use device that is physician applied for ambulatory, continuous, home-based therapy. It is to be percutaneously implanted into the cranial and/or peripheral nerves and corresponding neural vascular bundles of the auricular and periauricular areas as ascertained by the disclosed method of evaluating and implanting of the electrode/needle array. This includes transillumination of the auricular and periauricular tissues and surrounding neurovascular anatomy. The auricular peripheral nerve stimulator system allows for continuous, intermittent neural stimulation for up to five days.

In another embodiment, electrode/needle array implantation into the skin of the ear allows for direct access to branches of cranial nerves V, VII, IX, and X as well as branches of the occipital nerves. Direct access to the arterial branches of the head and neck are accessible and reduction of sympathetic stimulation results in an increase of vascular flow rate, reduction of vascular resistance and increase of perfusion. The arterial branches of the superficial temporal artery and the posterior auricular artery form a rich interconnecting complex network the terminal branches of which anastomose throughout the ear.

In another embodiment, the auricular peripheral nerve stimulator alters production and utilization of serotonin via vagal stimulation, and meningovascular dilation secondary to decreased sympathetic (or increased parasympathetic) tone.

The actual location and determination of needle placement (called points) is based upon tradition and theory of acupuncture. While the ascribed "points" may vary, depending upon the type of acupuncture to which one prescribes, the rationale and needle placement varies little and the theory is the same.

The addition of electrical stimulation to the individual, non-connected needles does not alter the rationale and the location of application is still based upon the original theory. The addition of electricity, while considered an enhancement, still falls within the realm of auricular acupuncture.

The present invention provides methods not based upon acupuncture technique or "points" but rather peripheral nerve field stimulation, anatomical location of cranial nerves, peripheral nerves, arterial branches and/or neurovascular bundles, and energy transfer based upon accepted laws of energy transfer in human tissue. Peripheral nerve field stimulation is an accepted procedure for the affecting of targeted nerves to alter pain transmission on a local (peripheral) and CNS (central nervous system) level. PNFS is commonly used in the occipital nerves (branches of the cervical nerves) for headache control, and the femoral nerve of the leg for control of phantom limb pain, stump pain, and other types of peripheral pain. The PNFS technique is based upon neuro-anatomy, blood vessel anatomy, proximity of the electrodes to the actual nerves being stimulated, and verification of electrode proximity.

Without wishing to be bound by theory, the method of auricular application of PNFS relies on the fact that located within the ear are cranial nerves V, VII, IX, X which anastomose (connect) directly into the brain and branches of the greater and lesser occipital nerves anastomosing directly into the cervical spine. There are distinct areas of the auricle on both the dorsal and ventral aspect which carry a predominance/concentration of the cranial nerves, peripheral nerves, arterial branches, and neurovascular bundles.

Branches of the superior temporal artery and the posterior auricular artery are found within the external ear, entering from the anterior (ventral) and posterior (dorsal) aspect of the ear. These arteries converge in the lobe, branching eventually into the cellular level forming a complex, interconnecting network branching according to Mandelbrot's set.

For a stimulation therapy in the case of certain disorders or illnesses and, e.g., for achieving a homogenous sensation at the entire ear it is advantageous to continuously change the polarity of the therapeutic currents. For this, a configuration of the inventive device is provided which is characterized in that during a current flow of the therapeutic currents fed to the individual stimulation electrodes, these stimulation electrodes, at the time considered in each case, have polarities which differ from each other with regard to a reference potential point which is connected with the therapeutic current circuits. This configuration results also in an at least partial relief of a reference electrode connected to the reference potential point from the therapeutic currents flowing through the stimulation electrodes. This effect applies to an even greater extent to a refinement, which is characterized in that the therapeutic currents, which are fed to the individual stimulation electrodes which have polarities which differ from each other at the respectively considered time, compensate each other at the respectively considered time so that no therapeutic current flows through a reference electrode. In this manner, a reference electrode can be eliminated. It is further beneficial if it is provided that the control circuit—which is provided in the micro-computer circuit and which feeds a control signal to the amplifiers provided in the output channels, which said control signal, in a cyclical succession, forms time intervals in which a current flow to the stimulation electrodes takes place and time intervals in which the output channels are inactive, wherein in each case one current flow time interval and one inactive time interval together form one stimulation cycle, and wherein in the current flow time intervals, a therapeutic current flows in the form of a packet of successive pulses or in the form of a single pulse—causes a polarity reversal at each current flow time interval. It is preferably provided in this connection that the polarity reversal is caused within the current flow time intervals. This is often considered as being therapeutically beneficial.

As already mentioned above, it is advantageous for certain stimulation therapies, e.g. pain therapies for chronic disorders, to start with low values at the beginning of the treatment and to slowly increase the intensity of the stimulation to the full intended extent. For this, an embodiment of the device according to the invention is provided which is characterized in that the control circuit—which is provided in the micro-computer circuit and which feeds a control signal to the amplifiers provided in the output channels, which said signal, in a cyclical succession, forms time intervals in which a current flow to the stimulation electrodes takes place and time intervals in which the output channels are inactive, wherein in each case one current flow time interval and one inactive time interval together form one stimulation cycle—at the beginning of a stimulation cycle sequence formed by a multiplicity of successive stimulation cycles, continuously increases during a plurality of successive stimulation cycles from in each case one stimulation cycle to the next following stimulation cycle the intensity of the therapeutic current fed to a respectively considered stimulation electrode, the intensity being considered as average over the respective current flow time interval, and subsequently maintains during a multiplicity of successive stimulation cycles within their current flow time intervals the previously achieved level of intensity of the therapeutic currents. Thereby, the sensation of the stimulation as well as the effect of the treatment can be further improved if it is provided that at the end of the stimulation cycle sequence, the control circuit feeds a control signal to the amplifiers provided in the output channels, which said control signal continuously decreases from in each case one stimulation cycle to the next following stimulation cycle the intensity of the therapeutic current fed to a respectively considered stimulation electrode, the intensity being considered as average over the respective current flow time interval.

With regard to the energy supply of the device according to the invention, an embodiment is preferred which is characterized in that for supplying the amplifiers provided in the output channels, a voltage transformer with a bipolar output is provided which, for its part, is supplied by the battery provided in the device. In this manner, supplying the amplifiers can be carried out with a battery which is formed from only one cell or few cells and, in a given space, has a relatively high energy content which enables a stimulation operation over several days. Another extension of the treatment duration possible with the device can be achieved by minimizing the losses occurring in the mentioned voltage transformer. For this, a refinement of the aforementioned embodiment provides that in the connection supplying from the battery to the voltage transformer, a switching device is inserted which interrupts the supply during the current flow pauses present in the therapeutic current circuits as well as upon exceedance of a predefined limit value of the current drawn by the voltage transformer from the battery. Besides the energy-saving function, the switching device has the function of protection against overloading the battery and against exceeding predefined values of the therapeutic currents.

Another embodiment which is effective in terms of the best possible utilization of the energy contained in the supplying battery is characterized in that for supplying the micro-computer circuit, the digital-analog converter and potentially provided measurement signal circuits, a voltage transformer is provided which has an unipolar output and is connected to the battery, wherein said voltage transformer is bypassed with a Schottky diode and is activated only when the battery voltage falls, and delivers at its output a voltage that corresponds to the battery target voltage.

For setting the parameters of the therapeutic currents for the respective present treatment case, an embodiment of the device according to the invention is advantageous and preferred which is characterized in that the device has a wirelessly operating transmission device which is connected to the micro-computer circuit and serves, by means of an external control device, for entering parameters to be stored of the therapeutic currents provided for the respective treatment. Furthermore, it can advantageously be provided that the device has a wirelessly operating transmission device which is connected to the micro-computer circuit and serves for transmitting stored parameters of the therapeutic currents provided for the respective treatment to an external control and monitoring device.

Bilateral Approach

A protocol has been described to make use of device along with medications designed to promote comfort for an approximately 5-day period with the goal to get onto opioid antagonist therapy with a long-acting naltrexone product. Long-acting naltrexone currently comes in the form of a monthly depot injection, Vivitrol, and various naltrexone implants. A published study describes 85% of opioid withdrawal symptoms being controlled within 30 minutes. Residual symptoms are controlled using comfort medications described in protocol. (Journal of Addiction Medicine. Neuromodulation with BRIDGE is Associated with Reduction in Signs and Symptoms of Opioid Withdrawal-A Retrospective, Multisite Study.)

Mechanism of action of device is most likely from autonomic regulation from stimulating the Vagus Nerve promoting Parasympathetic activity. Imaging study in rats shows 65% reduction in neuronal firing of the Amygdala, the area of the brain which controls emotional tone which includes fear, terror, and anxiety. (Miranda A, Babygirija R. Neurostimulation with IBStim attenuates amygdala neurons and prevents post-inflammatory visceral and somatic hyperalgesia in rats. World Congress of pediatric gastroenterology, hepatology, and nutrition.)

Other possible mechanisms of action include disruption of ascending and descending pain tracks of the dorsal column, stimulation of Trigeminal nerve causing release of pain modulating neurochemicals of endorphin from para-aqueductal grey and serotonin from raphe nucleus.

Comfort medications are utilized within this period of detoxification because of presence of residual symptoms. Possible explanation of incomplete resolution of withdrawal symptoms can be explained by nerve attenuation during this period. Nerve attenuation can be described as the reduction of the amplitude of a signal, electric current, or action potential of a nerve.

Use Left Ear First

The left ear is the preferred site as the right sided auricular branches of the vagus nerve innervates the sinoatrial node of the heart and influences the heart rate. R-VNS seems to be an effective and alternative therapy in selected patients responding to L-VNS where a left-sided reimplantation is not possible. (1)

Nerve Attenuation

Because of possible nerve attenuation during this period, an approach has been described to take advantage of bilateral auricular and facial branches of Cranial Nerves.

Cardiac slowing in response to a standard electrical stimulus applied to the vagus (1-2 Hz for 10 s) was potentiated after a 2-min high frequency stimulation (10 Hz). This potentiation of cardiac vagal action was abolished after a 1-hour period of repetitive vagal stimulation. (Cardiac vagal effects in the toad are attenuated by repetitive vagal stimulation. Neuropeptides. 1993 September; 25 (3): 193-8.)

Bilateral Approach

The protocol would require two identical pre-programmed devices implanted bilaterally. The first device would be implanted and be programmed with alternating times of stimulation. Once the first device is programmed to stop stimulation, to prevent nerve attenuation, a second device would be installed in the opposite ear. The second device would take over stimulation for the same period while the first device is off.

Since nerve attenuation can be seen between 1-6 hours of placement of the device it is suggested that both devices be programmed with identical alternating stimulations for 1-6 hours. We suggest that 2 hours on/off schedule has been effective and will described as the example below.

For example, a person presents in moderate to severe opioid withdrawal. Device #1 is installed, and patient is either supervised in the clinic for the next 2 hours or asked to come back within 2 hours to prepare for installation of device #2. It is important to implant device #2 exactly when device #1 is programmed to be off.

After 2 hours the patient presents again to the clinic and device #2 is installed in the opposite ear. Device #1 will not be taken off. Both devices will be worn for the total of 120 hours (5 days).

Both devices are identically pre-programmed, in this example, for 2 hours of alternating electrical stimulation. This approach can minimize nerve attenuation and use of comfort medications.

Additional Methods

In one or more embodiments, the methods of the present invention use the electrical stimulation device to get a patient onto the lowest dosage level of buprenorphine.

Use of suboxone can be a problem, if used too early, as it causes a precipitated withdrawal. Buprenorphine/naloxone (antagonist) combination drug, sold under the brand name Suboxone among others, is a fixed-dose combination medication that includes buprenorphine and naloxone. Naloxone, sold under the brand name Narcan among others, is a medication used to block the effects of opioids. Naloxone is a non-selective and competitive opioid receptor antagonist. It works by reversing the depression of the central nervous system and respiratory system caused by opioids.

Once used, it is a challenge to get a patient off of suboxone at high dose. Therefore, if put on the lowest dose, there is a much better chance to get off the drug in the end.

In one or more embodiments, the methods of the present invention provide for:
1. Put the patient on the electrical stimulation device (bridge) to control symptoms for 4-5 days; may need two devices for long-acting drugs;
2. Administer non-narcotic medications-start day 2 and administer until detox is complete (around 5 days) e.g., naltrexone is active in Vivitrol=antagonist a. Can't use unless completely detoxed; here the bridge allows early start
3. Administer comfort medications that focus on symptom control
4. Introduce lowest buprenorphine-(Suboxone) start day 2 or 3 when see moderate withdrawal symptoms; can trigger withdrawal is start too early
   a. On 3rd day, either detoxed or moderate withdrawal and introduce buprenorphine
5. Stabilized
6. Methadone is very long-acting so 2-3 times to get off
7. Short-acting so needs 2-3 doses All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A method of treating drug or alcohol abuse, addiction or dependency or preventing relapse use of drug or alcohol or addictive behavior comprising:
   (a) treating a subject with an electrical stimulation device comprising an auricular or peri-auricular electro-acupuncture or neurostimulation device comprising one or more electrodes, which is accompanied by,
   (b) administering to the subject in need thereof a therapeutically effective amount for at least one day with a composition consisting of at least one non-narcotic detoxification agent including one of robaxin, probanthine, gabapentin, ropinirole, and trazodone, which is accompanied by,
   (c) administering to the subject a drug screen, followed by,
   (d) repeating, in response to the drug screen testing positive for opioids and/or opiates, the steps of treating the subject with the electrical stimulation device, administering to the subject of the therapeutically effective amount of the composition, and administering to the subject the drug screen, and
   (e) administering, in response to the drug screen testing negative for opioids and opiates, to the subject in need thereof a therapeutically effective amount of an opioid antagonist,
   wherein the electrical stimulation device comprising an electrical signal generator configured to generate electrical stimulation pulses having a repetition frequency of 0.5 to 100 Hz and a duty cycle of 10 to 90%, and wherein both steps (a) and (b) treatment are carried out contemporaneously for about 1 to about 7 days.

2. The method according to claim 1, wherein the addictive behavior is exhibited by the subject, following exposure of the subject to at least one stimulus, which induces in the subject an addictive behavior.

3. The method according to claim 2, wherein the at least one non-narcotic detoxification agent comprises at least one sedative.

4. The method according to claim 3, wherein the at least one sedative comprises antipsychotics, atypical antipsychotics, alpidem, amobarbital, antihistamines, barbiturates, benzodiazepines, chloral hydrate, chlorazepate, chlordiazepoxide, clonazepam, clonidine, diethyl ether, dimenhydrinate, diphenhydramine, doxylamine, ethchlorvynol, flunitrazepam, gamma-hydroxybutyrate, glutethimide, herbal sedatives, imidazopyridines, kava, lorazepam, meprobamate, methaqualone, methyl trichloride, methyprylon, phenabarbitol, pentobarbital, promethazine, pyrazolopyrimidines, seroquel, secobarbital, tiagabine, tranquilers, zaleplon, zolpidem, a pharmaceutically acceptable salt or complex thereof, a combination thereof, and a pharmaceutical composition comprising the same.

5. The method according to claim 4, wherein the at least one sedative is selected from the group consisting of benzodiazepines and Z-drugs.

6. The method according to claim 5, wherein the opioid antagonist comprises 7-benzylidenenaltrexone, beta-funaltrexamine, buprenorphine, butorphanol, chlornaltrexamine, clocinnamox, connective tissue-activating peptide, cyclazocine, diprenorphine, ICI 154129, levallorphan, lofexidine, meptazinol, methylnaltrexone, N,N-diallyl-tyrosyl-alpha-aminoisobutyric acid-phenylalanyl-leucine, nalbuphine, nalmefene, nalorphine, naloxone, naltrexone, or naltrindole, or mixtures or combinations thereof.

7. The method according to claim 6, wherein step (c) comprises administering to the subject a controlled release pharmaceutical composition comprising the opioid antagonist.

8. The method according to claim 7, wherein the controlled release pharmaceutical composition releases the opioid antagonist over a period of more than about 4 to about 24 weeks.

9. The method according to claim 8, wherein the addiction is a physical dependence to an addictive agent or to an addictive behavior.

10. The method according to claim 9, wherein the addictive agent is a pain-killer or a combination of pain-killers.

11. The method according to claim 10, wherein the pain-killer is selected from the group consisting of alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol and tilidine.

12. The method according to claim 9, wherein the addictive agent is selected from the group consisting of alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofenitanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thehaine, Lildine and tramadol.

13. The method according to claim 9, wherein the addictive behavior is selected from the group consisting of obsessive-compulsive disorder, compulsive spending and/or gambling, pathological overeating, pathological use of electronic devices and, communication devices such as cellular phones, pathological use of electronic video games, addiction to pornography and sex, eating disorders such as anorexia and bulimia, kleptomania, pyromania, compulsive over-exercising and overworking.

14. The method according to claim 1, wherein the electrical signal generator is configured to generate electrical stimulation pulses having a repetition frequency of 1-10 Hz, and a duty cycle of 40 to 60%.

15. The method according to claim 14, wherein the stimulation pulses are generated at a constant current amplitude.

16. The method according to claim 1, wherein the electrodes are adapted to alternatively stimulate the left and right-side nerves.

17. The method according to claim 14, wherein the addictive agent is selected from the group consisting of alcohol, caffeine, nicotine, cannabis and cannabis derivatives, opiates and morphine-like compounds, phencyclidine and phencyclidine-like compounds, sedative hypnotics, psychostimulants, amphetamines and amphetamine-related drugs, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

18. The method according to claim 17, wherein the addictive agent is cocaine.

19. A method of treating post-acute-withdrawal syndrome (PAWS), in a subject, comprising:
(i) treating a subject with an electrical stimulation device comprising an auricular or peri-auricular electro-acupuncture or neurostimulation device comprising one or more electrodes, which is accompanied by,
(ii) administering to the subject in need thereof a therapeutically effective amount for at least one day with a composition consisting of at least one non-narcotic detoxification agent, including one of robaxin, probanthine, gabapentin, ropinirole, and trazodone which is accompanied by,
(iii) administering to the subject a drug screen for opioids and/or opiates, followed by,
(iv) repeating, in response to the drug screen testing positive, the steps of treating the subject with the electrical stimulation device, administering to the subject of the therapeutically effective amount of the composition, and administering to the subject the drug screen, and
(v) administering, in response to the drug screen testing negative, to the subject in need thereof a therapeutically effective amount of an opioid antagonist;
wherein the electrical stimulation device comprising an electrical signal generator configured to generate electrical stimulation pulses having a repetition frequency of 0.5 to 100 Hz and a duty cycle of 10 to 90%, and wherein both steps (i) and (ii) treatment are carried out contemporaneously for at least one day.

\* \* \* \* \*